United States Patent
Yuzawa

(10) Patent No.: US 12,053,290 B2
(45) Date of Patent: Aug. 6, 2024

(54) BRAIN ATLAS CREATION APPARATUS, BRAIN ATLAS CREATION METHOD, AND BRAIN ATLAS CREATION PROGRAM

(71) Applicant: FUJIFILM Corporation, Tokyo (JP)

(72) Inventor: Takuya Yuzawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 618 days.

(21) Appl. No.: 17/211,855

(22) Filed: Mar. 25, 2021

(65) Prior Publication Data

US 2021/0209406 A1 Jul. 8, 2021

Related U.S. Application Data

(63) Continuation of application No. PCT/JP2019/022055, filed on Jun. 3, 2019.

(30) Foreign Application Priority Data

Sep. 28, 2018 (JP) ................................ 2018-184407

(51) Int. Cl.
*A61B 5/00* (2006.01)
*G06F 3/0486* (2013.01)
(Continued)

(52) U.S. Cl.
CPC .......... *A61B 5/4064* (2013.01); *A61B 5/7264* (2013.01); *G06F 3/0486* (2013.01);
(Continued)

(58) Field of Classification Search
CPC ... A61B 5/4064; A61B 5/7264; A61B 5/0042; A61B 5/055; A61B 6/032; A61B 6/037;
(Continued)

(56) References Cited

U.S. PATENT DOCUMENTS

| 10,290,105 B2 | 5/2019 | Ishii et al. |
| 10,438,380 B2 | 10/2019 | Hu et al. |

(Continued)

FOREIGN PATENT DOCUMENTS

| JP | 2005044299 | 2/2005 |
| JP | 2017023457 | 2/2017 |

(Continued)

OTHER PUBLICATIONS

"Office Action of Japan Counterpart Application" with English translation thereof, issued on Nov. 9, 2021, p. 1-p. 8.

(Continued)

*Primary Examiner* — Gabriel I Garcia
(74) *Attorney, Agent, or Firm* — JCIPRNET

(57) ABSTRACT

The brain atlas creation apparatus includes: an image acquisition unit that acquires a brain image; a section setting unit that classifies a brain area in the brain image acquired by the image acquisition unit into a plurality of layers from a major category which is a higher layer to a minor category which is a lower layer and sets a brain section for each category; and a display control unit that performs control to switch the brain image for each category classified by the section setting unit and to display the brain image on a display unit.

10 Claims, 7 Drawing Sheets

(51) Int. Cl.
*G06F 3/14* (2006.01)
*G06F 18/2431* (2023.01)
*A61B 5/055* (2006.01)
*A61B 6/03* (2006.01)
*A61B 6/50* (2024.01)

(52) U.S. Cl.
CPC ............ *G06F 3/14* (2013.01); *G06F 18/2431* (2023.01); *A61B 5/0042* (2013.01); *A61B 5/055* (2013.01); *A61B 6/032* (2013.01); *A61B 6/037* (2013.01); *A61B 6/501* (2013.01); *G06V 2201/031* (2022.01)

(58) Field of Classification Search
CPC ... A61B 6/501; G06F 18/2431; G06F 3/0486; G06F 3/14; G06V 2201/031
USPC ....................................................... 382/128
See application file for complete search history.

(56) References Cited

U.S. PATENT DOCUMENTS

| | | | | |
|---|---|---|---|---|
| 11,403,755 | B2* | 8/2022 | Wang | ..................... A61B 10/00 |
| 2012/0184560 | A1* | 7/2012 | Wong | ................... A61K 31/404 |
| | | | | 435/7.1 |
| 2013/0178693 | A1* | 7/2013 | Neuvonen | ............ A61B 5/7425 |
| | | | | 600/13 |
| 2014/0161338 | A1* | 6/2014 | Machado | ................ G06T 7/344 |
| | | | | 382/131 |
| 2017/0071497 | A1 | 3/2017 | Yamagata et al. | |
| 2018/0144467 | A1* | 5/2018 | Sofka | ................... A61B 5/4064 |
| 2019/0362835 | A1* | 11/2019 | Sreenivasan | ........... G06N 3/044 |
| 2020/0111207 | A1* | 4/2020 | Peng | ........................ G06T 7/11 |
| 2020/0230413 | A1* | 7/2020 | Madhavan | ............. A61B 5/055 |
| 2020/0380681 | A1* | 12/2020 | Park | ....................... G06T 7/149 |

FOREIGN PATENT DOCUMENTS

| | | |
|---|---|---|
| JP | 2017051599 | 3/2017 |
| JP | 2018505705 | 3/2018 |

OTHER PUBLICATIONS

"Office Action of Japan Counterpart Application" with English translation thereof, issued on Aug. 10, 2021, p. 1-p. 6.
"International Search Report (Form PCT/ISA/210) of PCT/JP2019/022055," mailed on Aug. 13, 2019, with English translation thereof, pp. 1-5.
"Written Opinion of the International Searching Authority (Form PCT/ISA/237) of PCT/JP2019/022055," mailed on Aug. 13, 2019, with English translation thereof, pp. 1-12.
Akira Magazine, "Story of the cerebral cortex", Sep. 23, 2018, Available at: https://akira3132.info/cerebral_cortex.html.
Hatena, "How to use brain images FOR PT, OT, STJ", Jan. 24, 2017, Available at: http://tsukasaseikatsu.hatenablog.com/?page=1485306108.

* cited by examiner

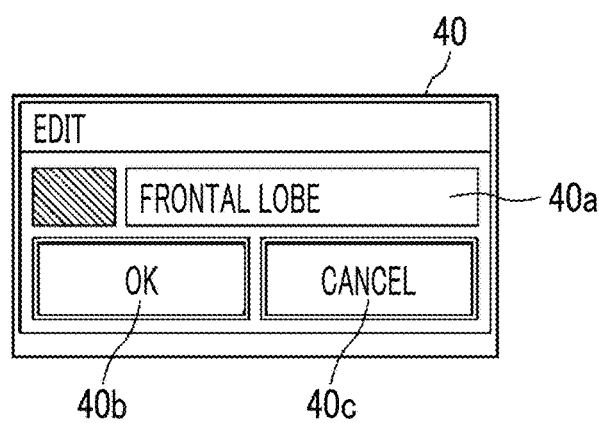

BRAIN ATLAS CREATION APPARATUS, BRAIN ATLAS CREATION METHOD, AND BRAIN ATLAS CREATION PROGRAM

CROSS-REFERENCE TO RELATED APPLICATION

The present application is a continuation application of International Application No. PCT/JP2019/022055, filed Jun. 3, 2019, which claims priority to Japanese Patent Application No. 2018-184407, filed Sep. 28, 2018. The contents of these applications are incorporated herein by reference in their entirety.

BACKGROUND

Field of the Invention

The present disclosure relates to a brain atlas creation apparatus, a brain atlas creation method, and a brain atlas creation program.

Related Art

In recent years, advances in medical apparatuses, such as a computed tomography (CT) apparatus and a magnetic resonance imaging (MM) apparatus, have made it possible to perform image diagnosis using high-resolution medical images with higher quality. In particular, image diagnosis methods have become indispensable as a biomarker for dementia diseases. Among them, image diagnosis using magnetic resonance (MR) images which can evaluate a detailed brain structure can capture brain atrophy due to neuronal loss. Therefore, it is possible to perform early detection, differential diagnosis, and progression evaluation on the dementia diseases. Therefore, various methods for supporting image diagnosis on dementia diseases using medical images have been proposed.

On the other hand, in image diagnosis on Alzheimer-type dementia, a method is used which examines the degree of parahippocampal gyms atrophy that is characteristic of Alzheimer-type dementia as compared to healthy brain images, using software called Voxel-based Specific Regional Analysis System for Alzheimer's Disease (VSRAD). Further, for example, JP2017-023457A discloses a method which creates an estimated image of the atrophied brain obtained by estimating atrophy due to the aging of a subject, using image data obtained by capturing the image of the brain of the subject and atrophy parameters which are parameters in image processing for performing brain atrophy processing, and compares the estimated image with the brain image of the subject to evaluate brain atrophy caused by aging and brain atrophy caused by lesions. JP2018-505705A discloses a method which performs a projection process on three-dimensional image data of the brain using a minimum intensity projection method to generate a projection image of the brain and displays the projection image together with an image of the brain surface, in order to reduce the labor of doctors in diagnosis on, for example, brain dementia using medical images.

The method using VSRAD has a problem that it is not capable of absorbing a change due to an individual difference between patients and it is not quantitative. Therefore, a method has been proposed which extracts a storage section in a brain image and compares the volume of the same section of the brain image of the same subject captured in the past. The brain section in the brain image is extracted in the minimum unit (hereinafter, referred to as a minor category) of the section such as "the hippocampus of the left brain". However, there are the following requests depending on the state of the lesion and the doctor: a request that "the doctor wants to observe brain atrophy as a whole in the limbic system and other areas, that is, in the medium and major categories higher than the minor category"; and a request that "the doctor wants to observe brain atrophy as a whole in functional categories instead of anatomical categories". In addition, since the definition of the brain section may vary depending on the literature, it is difficult to uniformly set the definition of the brain section.

SUMMARY

The present disclosure has been made in view of the above-mentioned problems, and an object of the present disclosure is to visualize any brain section.

A brain atlas creation apparatus according to the present disclosure comprises: an image acquisition unit that acquires a brain image; a section setting unit that classifies a brain area in the brain image acquired by the image acquisition unit into a plurality of layers from a major category which is a higher layer to a minor category which is a lower layer and sets a brain section for each category; and a display control unit that performs control to switch the brain image for each category classified by the section setting unit and to display the brain image on a display unit.

In addition, the brain atlas creation apparatus according to the present disclosure may further comprise a receiving unit that receives the section set by the section setting unit for each category. The display control unit may perform control to switch the section received by the receiving unit to the brain image in a category lower than a category, to which the section belongs, and to display the brain image on the display unit.

Further, the brain atlas creation apparatus according to the present disclosure may further comprise a receiving unit that receives the section set by the section setting unit for each category; and a category change unit that changes a category higher than a category, to which the section received by the receiving unit belongs, in the section.

Furthermore, in the brain atlas creation apparatus according to the present disclosure, the display control unit may perform control to switch the section received by the receiving unit to the brain image in a category lower than the category, to which the section belongs, and to display the brain image on the display unit.

Moreover, in the brain atlas creation apparatus according to the present disclosure, the display control unit may perform control to display at least a portion of the area in a lower category and at least a portion of the area in a category higher than the lower category on the display unit. The category change unit may drag and drop the section received by the receiving unit in the lower category onto a section set in the higher category to change the higher category of the received section to the category of the dragged and dropped section.

In addition, in the brain atlas creation apparatus according to the present disclosure, the display control unit may perform control to display, on the display unit, a list of names of the sections of the brain for each category in a tree shape. The category change unit may drag and drop the name of a section selected in the list to the name of a section set in the category higher than the category, to which the section belongs, to change the higher category.

Further, in the brain atlas creation apparatus according to the present disclosure, the display control unit may perform control to display, on the display unit, a name of the category higher than the category to which the section received by the receiving unit belongs. The category change unit may change the name of the higher category to change the higher category of the received section.

Furthermore, in the brain atlas creation apparatus according to the present disclosure, the category change unit may be capable of changing the category only in adjacent sections.

According to the present disclosure, there is provided a brain atlas creation method comprising: acquiring a brain image; classifying a brain area in the acquired brain image into a plurality of layers from a major category which is a higher layer to a minor category which is a lower layer and setting a brain section for each category; and performing control to switch the brain image for each classified category and to display the brain image on a display unit.

In addition, a program that causes a computer to perform the brain atlas creation method according to the present disclosure may be provided.

Another brain atlas creation apparatus according to the present disclosure comprises: a memory that stores commands to be executed by a computer; and a processor configured to execute the stored commands. The processor acquires a brain image, classifies a brain area in the acquired brain image into a plurality of layers from a major category which is a higher layer to a minor category which is a lower layer, sets a brain section for each category, and performs control to switch the brain image for each classified category and to display the brain image on a display unit.

According to the brain atlas creation apparatus, the brain atlas creation method, and the brain atlas creation program of the present disclosure, it is possible to visualize any brain section.

BRIEF DESCRIPTION OF THE DRAWINGS

FIG. 13 is a diagram illustrating an operation of changing a category in the brain section list.

FIG. 14 is a diagram illustrating an operation of changing a category in the brain section list.

FIG. 15 is a diagram illustrating an operation of changing a category in the brain section list.

DETAILED DESCRIPTION

Figure 1:
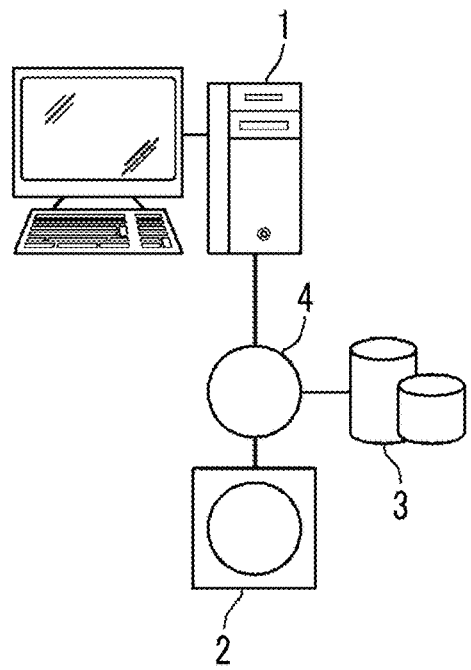
FIG. 1 is a hardware configuration diagram illustrating the outline of a diagnosis support system to which a brain atlas creation apparatus according to an embodiment of the present disclosure is applied.

Hereinafter, a first embodiment of the present disclosure will be described with reference to the drawings. FIG. 1 is a hardware configuration diagram illustrating the outline of a diagnosis support system to which a brain atlas creation apparatus according to an embodiment of the present disclosure is applied. As illustrated in FIG. 1, in the diagnosis support system, a brain atlas creation apparatus 1, a three-dimensional imaging apparatus 2, and an image storage server 3 according to this embodiment are connected so as to communicate with each other through a network 4.

The three-dimensional imaging apparatus 2 is an apparatus that captures an image of a diagnosis target part of a subject to generate a three-dimensional image indicating the part and is specifically a CT apparatus, an MRI apparatus, a positron emission tomography (PET) apparatus, or the like. A medical image generated by the three-dimensional imaging apparatus 2 is transmitted to the image storage server 3 and is then stored therein. In this embodiment, the diagnosis target part of a patient as the subject is the brain.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including image data of the three-dimensional image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM). Further, in this embodiment, the image storage server 3 stores a three-dimensional image of the head.

The brain atlas creation apparatus 1 is implemented by installing a brain atlas creation program according to the present disclosure in one computer. The computer may be a workstation or a personal computer that is directly operated by a doctor who performs diagnosis or may be a server computer that is connected to them through the network. The brain atlas creation program is recorded on a recording medium, such as a digital versatile disc (DVD) or a compact disc read only memory (CD-ROM), is distributed, and is then installed in the computer from the recording medium. Alternatively, the brain atlas creation program is stored in a storage device of a server computer connected to the network or a network storage so as to be accessed from the outside, is downloaded to the computer used by the doctor on request, and is then installed in the computer.

Figure 2:
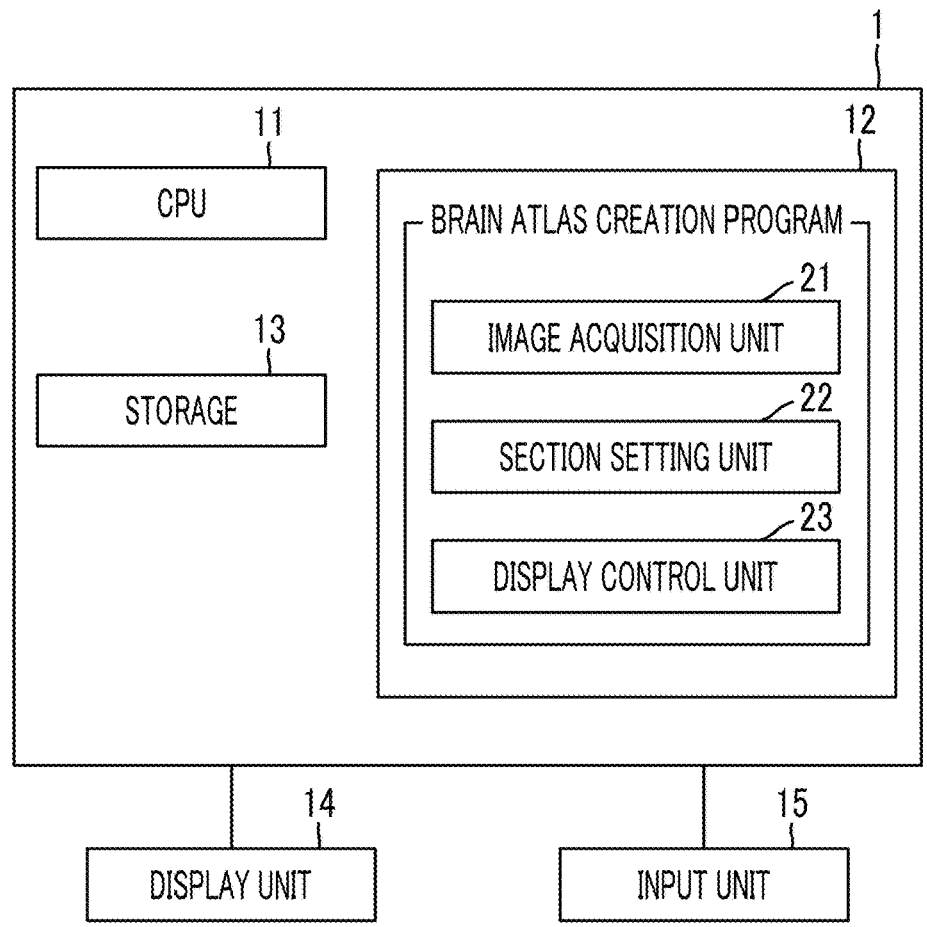
FIG. 2 is a schematic block diagram illustrating a configuration of a brain atlas creation apparatus according to a first embodiment of the present disclosure.

FIG. 2 is a diagram illustrating a schematic configuration of the brain atlas creation apparatus according to the first embodiment of the present disclosure which is implemented by installing the brain atlas creation program in the computer. As illustrated in FIG. 2, the brain atlas creation apparatus 1 comprises a central processing unit (CPU) 11, a memory 12, and a storage 13 as the configuration of a standard workstation. In addition, a display unit 14 consisting of, for example, a liquid crystal display and an input unit 15 consisting of, for example, a keyboard and a mouse are connected to the brain atlas creation apparatus 1. The input unit 15 receives various setting inputs from the user. In addition, a touch panel may be used so as to function as both the display unit 14 and the input unit 15.

The storage 13 consists of, for example, a hard disk drive and a solid state drive (SSD). The storage 13 stores various kinds of information including the medical images of the subject and information required for processes which are acquired from the image storage server 3 through the network 4.

Further, the memory 12 stores the brain atlas creation program. The brain atlas creation program defines the following processes as the processes to be executed by the CPU 11: an image acquisition process of acquiring a brain image; a section setting process of classifying a brain area of the acquired brain image into a plurality of layers from a major category which is a higher layer to a minor category which is a lower layer and setting a brain section for each category; and a display control process of performing control to switch the brain image for each classified category and to display the brain image on the display unit.

Then, the CPU 11 performs these processes according to the program such that the computer functions as an image acquisition unit 21, a section setting unit 22, and a display control unit 23.

The image acquisition unit 21 acquires a brain image. Here, the brain image includes a standard brain image in addition to the three-dimensional image of the brain of the subject generated by the three-dimensional imaging apparatus 2. The standard brain image can be created by using, for example, a head CT image, a head MR image, and a head PET image of any subject captured in the past. Specifically, the image acquisition unit 21 acquires at least one three-dimensional image among the head CT images, the head MR images, and the head PET image of a plurality of subjects from the image storage server 3 and acquires the average of the three-dimensional images as the standard brain image.

In addition, in the first embodiment, the image acquisition unit 21 acquires the standard brain image as described above. However, the technology of the present disclosure is not limited thereto. For example, the image acquisition unit 21 may acquire, as the standard brain image, a computer graphics (CG) image generated so as to be similar to the image of the brain of the subject from an external storage unit. In addition, a three-dimensional image created on the basis of three-dimensional brain MR images, such as the Talairach standard brain atlas, the Montreal Neurological Institute (MNI) template developed by the Montreal Neurological Institute, and the Human Brain Atlas (HBA), may be acquired as the standard brain image from the external storage unit.

Further, the image acquisition unit 21 acquires the brain image of the subject generated by the three-dimensional imaging apparatus 2 from the image storage server 3. In a case in which the brain image has already been stored in the storage 13, the image acquisition unit 21 may acquire the brain image from the storage 13.

The section setting unit 22 classifies a brain area of the brain image acquired by the image acquisition unit 21 into a plurality of layers from the major category which is the higher layer to the minor category which is the lower layer and sets the brain section for each category. In addition, the brain sections are set according to the anatomical meaning of the brain. Specifically, in this embodiment, eight sections of the cerebral cortex, the cerebral medulla, the basal ganglion, the cerebellum, the diencephalon, the cerebral ventricle, the brain stem, and the blood vessels are set as the major category. As a medium category, a plurality of sections are set in each of four sections of the major category. For example, six sections of the frontal lobe, the parietal lobe, the temporal lobe, the occipital lobe, the limbic system, and others are set in the cerebral cortex.

In addition, as the minor category, a plurality of sections are set in each section of the medium category. For example, 11 sections of the superior frontal gyms, the rostral middle frontal gyms, the caudal middle frontal gyms, the pars opercularis, the trigone, the orbital part, the lateral orbitofrontal cortex, the medial orbitofrontal cortex, the frontal pole, the precentral gyms, and the paracentral gyms are set in the frontal lobe.

Further, a method for setting the sections in the brain area by the section setting unit 22 is not limited to the above. For example, there may be no maximum classification. Furthermore, the medium category may be further classified into a plurality of layers. In this case, for example, the brain area is classified into layers of an upper medium category, a medium category, and a lower medium category in order from the higher layer. In addition, the number of layers is not limited to 3, 4, and 5, and the brain area may have any number of layers as long as the number of layers is two or more.

The brain sections for each category set by the section setting unit 22 as described above are stored in the storage 13 as section information including the name of each section, the coordinate value of each section, and the volume value of each section.

Further, in this embodiment, the section setting unit 22 sets the brain sections as described above. However, the technology of the present disclosure is not limited thereto. For example, the brain sections may be set by anatomical areas distinguished by known anatomical structures, Brodmann's areas that are cytoarchitecturally distinguished, arterial innervation areas, nerve distribution areas distinguished according to the category of cranial nerves, and the like.

Figure 3:
FIG. 3 is a diagram illustrating an example of the display of a brain atlas image in a major category.
Figure 4:
FIG. 4 is a diagram illustrating an example of the display of a brain atlas image in a medium category.
Figure 5:
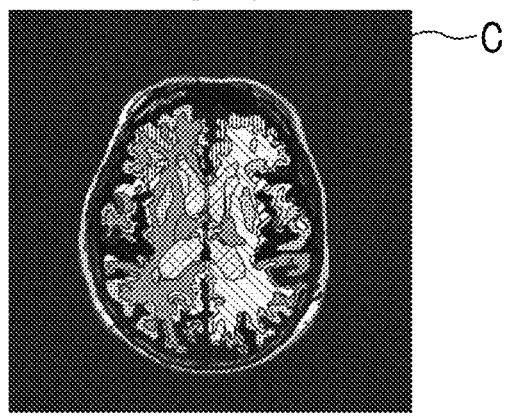
FIG. 5 is a diagram illustrating an example of the display of a brain atlas image in a minor category.

The display control unit 23 performs control to switch the brain image for each classified category and to display the brain image on the display unit 14. FIG. 3 is a diagram illustrating an example of the display of a major-category brain atlas image A. FIG. 4 is a diagram illustrating an example of the display of a medium-category brain atlas image B. FIG. 5 is a diagram illustrating an example of the display of a minor-category brain atlas image C. Here, the brain atlas image means an image in which the sections of the brain area are set in the brain image. Further, in FIGS. 3 to 5, a tomographic image of the brain is displayed as an example of the brain atlas image. Furthermore, in FIGS. 3 to 5, different display aspects indicate different sections.

In a case in which the display control unit 23 receives a brain image switching instruction input by the user through the input unit 15, for example, it switches the major-category brain atlas image A illustrated in FIG. 3, the medium-category brain atlas image B illustrated in FIG. 4, and the minor-category brain atlas image C illustrated in FIG. 5 and displays the brain atlas images on the display unit 14.

In addition, the display control unit 23 displays, as an initial setting, the major-category brain atlas image A illustrated in FIG. 3 on the display unit 14. Then, for example, in a case in which the user clicks the mouse as the input unit 15 on the major-category brain atlas image A illustrated in FIG. 3, the display control unit 23 displays the medium-category brain atlas image B illustrated in FIG. 4 on the display unit 14. Similarly, for example, in a case in which the user clicks the mouse as the input unit 15 on the medium-category brain atlas image B illustrated in FIG. 4, the display control unit 23 displays the minor-category brain atlas image C illustrated in FIG. 5 on the display unit 14. Further, for example, in a case in which the user clicks the mouse as the input unit 15 on the minor-category brain atlas image C illustrated in FIG. 5, the display control unit 23 displays the major-category brain atlas image A illustrated in FIG. 3 on the display unit 14. In addition, the switching order of the brain atlas images in a case in which the click operation has been performed by the user is not limited to the above and may be appropriately changed.

In the first embodiment, the display control unit 23 may display a list of section information, such as the name of each section, the coordinate value of each section, and the volume value of each section in the category of the displayed brain atlas image, on the same screen of the display unit 14 as the brain atlas image in any of the categories illustrated in FIGS. 3 to 5.

Figure 6:
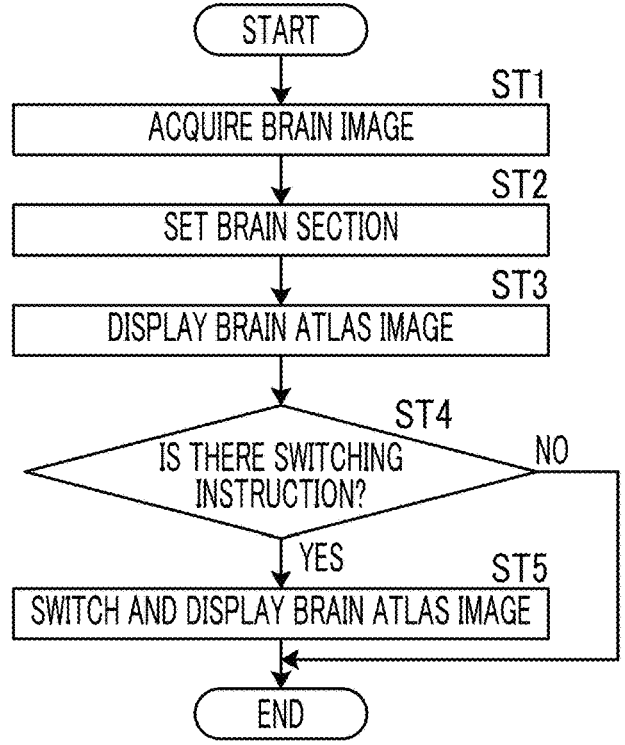
FIG. 6 is a flowchart illustrating a process performed in the first embodiment of the present disclosure.

Next, a process performed in the first embodiment will be described. FIG. 6 is a flowchart illustrating the process performed in the first embodiment. First, the image acquisition unit 21 acquires a brain image (Step ST1). Then, the section setting unit 22 sets the brain sections in the brain image acquired by the image acquisition unit 21 (Step ST2). Here, the section setting unit 22 acquires brain section information for each category stored in the storage 13 in advance and sets the brain sections on the basis of the section information.

Then, the display control unit 23 displays the brain atlas image, in which the brain sections have been set by the section setting unit 22, on the display unit 14 (Step ST3). Then, the display control unit 23 determines whether or not there is a switching instruction input by the user through the input unit 15 (Step ST4). In a case in which there is a switching instruction (Step ST4; YES), the display control unit 23 switches the brain atlas image and displays the brain atlas image on the display unit 14 as described above (Step ST5).

On the other hand, in Step ST4, in a case in which there is no switching instruction (Step ST4; NO), the display control unit 23 ends a series of processes while continuing to display the brain atlas image on the display unit 14. In this way, a series of processes according to the first embodiment is performed.

According to the first embodiment, any brain section can be visualized. This makes it possible for the user to check the brain section including the area desired to be observed in the brain image in the desired category among, for example, the major category, the medium category, and the minor category. Therefore, for example, in both the standard brain image and the brain image to be observed, in a case in which the atrophy ratio of the brain image to be observed to the standard brain image is measured in the displayed brain section, the technology of the present disclosure is applied to visualize the brain section set in the category desired by the user. Therefore, the user can intuitively understand the analysis information of the area that the user wants to observe. In addition, for example, in both the brain image to be observed and a brain image of the same subject as the brain image to be observed which was acquired in the past, in a case in which the atrophy ratio of the brain image to be observed to the past brain image is measured in the displayed brain section, the technology of the present disclosure is applied to visualize the brain section set in the category desired by the user. Therefore, the user can intuitively understand the analysis information of the area that the user wants to observe.

The standard brain image and the brain image to be observed, and the brain image to be observed and the brain image of the same subject as the brain image to be observed which was acquired in the past may be displayed on the same display unit 14. This makes it easier for the user to understand the area to be observed.

Figure 7:
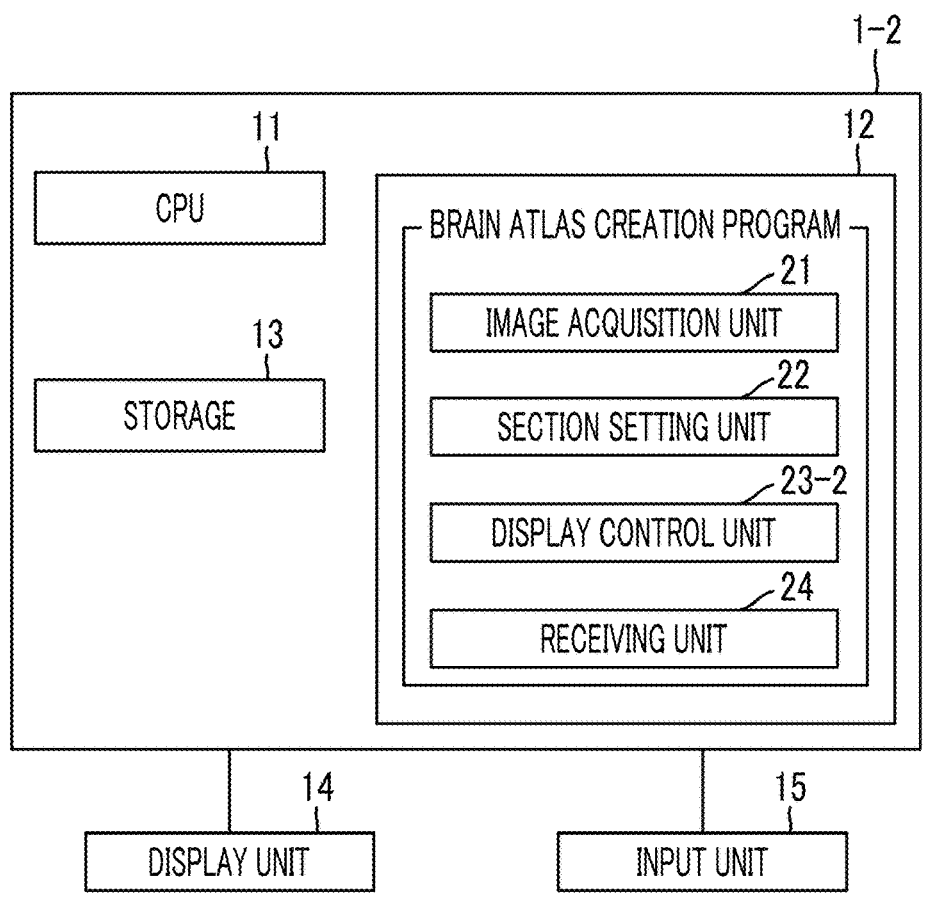
FIG. 7 is a schematic block diagram illustrating a configuration of a brain atlas creation apparatus according to a second embodiment of the present disclosure.

Next, a second embodiment of the present disclosure will be described with reference to the drawings. FIG. 7 is a diagram illustrating a schematic configuration of a brain atlas creation apparatus according to the second embodiment of the present disclosure. Since the brain atlas creation apparatus according to the second embodiment has substantially the same configuration as the brain atlas creation apparatus according to the first embodiment, the same configurations are denoted by the same reference numerals and the description thereof will be omitted. Only different components will be described in detail.

As illustrated in FIG. 7, a brain atlas creation apparatus 1-2 according to the second embodiment comprises a receiving unit 24 in addition to the configurations of the brain atlas creation apparatus 1 according to the first embodiment.

The receiving unit 24 receives the sections set by the section setting unit 22 for each category. Specifically, in a case in which the user clicks the mouse as the input unit 15 on the brain atlas image, the section including the clicked position is received. In addition, the receiving unit 24 is not limited to the clicking of the mouse. For example, in a case in which the display unit 14 is a touch panel that also functions as the input unit 15, the receiving unit 24 may receive the section directly selected by the user.

Figure 8:
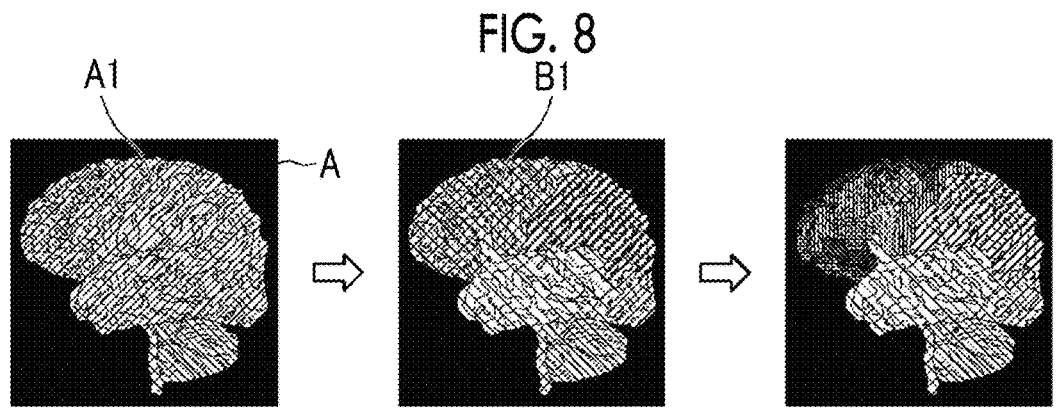
FIG. 8 is a diagram illustrating the switching of the display of a brain atlas.

A display control unit 23-2 according to the second embodiment performs control to switch the section received by the receiving unit 24 to a brain image in a category lower than the category, to which the received section belongs, and to display the brain image on the display unit 14. FIG. 8 is a diagram illustrating the switching of the display of the brain atlas.

As illustrated in FIG. 8, for example, in a case in which a cerebral cortex section A1 is clicked by the operation of the input unit 15 by the user in a major-category brain atlas image A as illustrated in the left diagram, the display control unit 23-2 switches the area of the clicked cerebral cortex section A1 to a medium-category brain atlas image and displays the medium-category brain atlas image as illustrated in the middle diagram. In this case, the display control unit 23-2 displays the entire brain area other than the cerebral cortex section A1 in gray. In addition, the displayed color is not limited to gray and may be, for example, black and white. Further, any display aspect may be used as long as it is different from the display aspect of the cerebral cortex section A1. Further, the display of the brain area other than the cerebral cortex section A1 may not be changed.

Furthermore, in a case in which a frontal lobe section B1 is clicked by the operation of the input unit 15 by the user in the medium-category brain atlas image displayed in the cerebral cortex section A1 as illustrated in the middle diagram of FIG. 8, the display control unit 23-2 switches the area of the clicked frontal lobe section B1 to a minor-category brain atlas image and displays the minor-category brain atlas image as illustrated in the right diagram. In this case, the display control unit 23-2 may display the entire brain area other than the frontal lobe section B1 in gray, similarly to the above.

Figure 9:
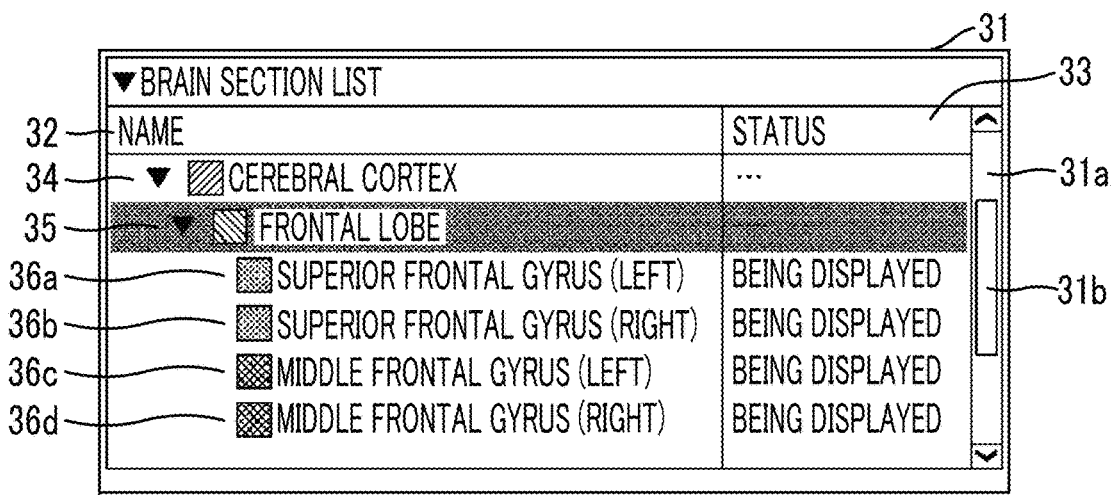
FIG. 9 is a diagram illustrating an example of a brain section list.

In the second embodiment, the display control unit 23-2 may display a list of section information, such as the name of each section, the coordinate value of each section, and the volume value of each section, in the category of the displayed brain atlas image on the same screen of the display unit 14 as the brain atlas image. FIG. 9 is a diagram illustrating an example of a brain section list.

As illustrated in FIG. 9, the display control unit 23-2 displays, as a brain section list 31, a list of information including the name 32 of the brain section and a status 33 indicating whether or not the brain section of this name is displayed. In addition, FIG. 9 illustrates an example of the brain section list 31 in a case in which the right diagram of FIG. 8 is displayed on the display unit 14, that is, in a case in which the area of the frontal lobe section B1 is displayed in the minor-category brain atlas image.

Therefore, as illustrated in FIG. 9, as the names of the brain sections, the cerebral cortex 34 in the major category to which the frontal lobe belongs, the frontal lobe 35, and the superior frontal gyms (left) 36a, the superior frontal gyms (right) 36b, the middle frontal gyms (left) 36c, and the middle frontal gyms (right) 36d which are the names of the sections set in the area of the frontal lobe section B1 are displayed. The status of the names is displayed as "being displayed". Further, in a case in which all of the names of the brain sections in the brain section list 31 are not capable of being displayed on the display unit 14, a scroll bar 31a is displayed as illustrated in FIG. 9 such that the user can move a display area by operating the input unit 15 to move a knob 31b in the scroll bar 31a. Furthermore, the display control unit 23-2 displays the name of the section received by the receiving unit 24 so as to be highlighted in the brain section list 31.

Figure 10:
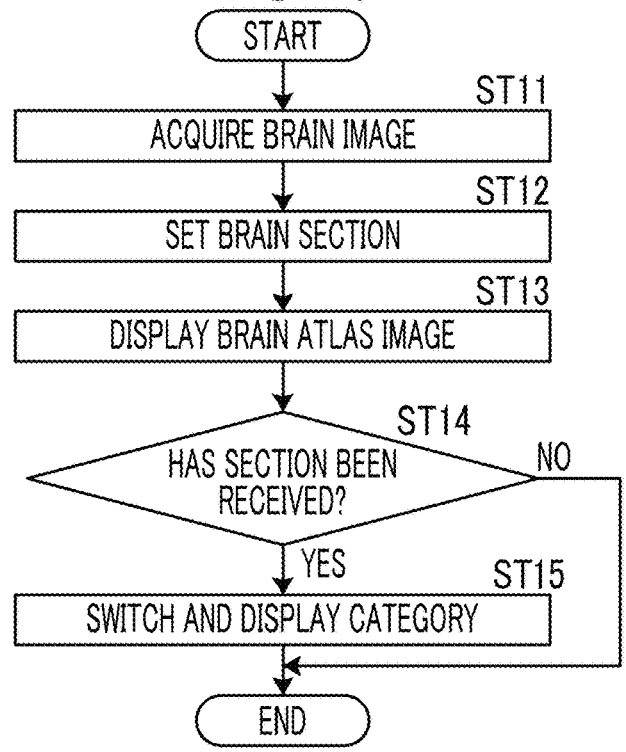
FIG. 10 is a flowchart illustrating a process performed in the second embodiment of the present disclosure.

Next, a process performed in the second embodiment will be described. FIG. 10 is a flowchart illustrating the process performed in the second embodiment. In addition, since a process in Steps ST11 to ST13 of the flowchart illustrated in FIG. 10 is the same as the process in Steps ST1 to ST3 of the flowchart illustrated in FIG. 6, the description thereof will be omitted for convenience.

In Step ST14, the receiving unit 24 determines whether or not a section has been received (Step ST14). In a case in which a section has been received (Step ST14; YES), the display control unit 23 switches the category of the section received by the receiving unit 24 and displays the category as described above (Step ST15). That is, the display control unit 23 switches the brain atlas image in the category lower than the category, to which the section received by the receiving unit 24 belongs, and displays the brain atlas image on the display unit 14.

On the other hand, in a case in which a section has not been received in Step ST4 (Step ST14; NO), the display control unit 23 ends a series of processes while continuing to display the brain atlas image on the display unit 14 without switching the category. In this way, a series of processes in the second embodiment is performed.

According to the second embodiment, any brain section can be visualized. This makes it possible for the user to check only the brain section including the area to be observed in the brain image in the desired category among, for example, the major category, the medium category, and the minor category. Therefore, for example, in both the standard brain image and the brain image to be observed, in a case in which the atrophy ratio of the brain image to be observed to the standard brain image is measured in the displayed brain section, the technology of the present disclosure is applied to visualize the brain section set in the category desired by the user. Therefore, the user can intuitively understand the analysis information of the area that the user wants to observe. In addition, for example, in both the brain image to be observed and a brain image of the same subject as the brain image to be observed which was acquired in the past, in a case in which the atrophy ratio of the brain image to be observed to the past brain image is measured in the displayed brain section, the technology of the present disclosure is applied to visualize the brain section set in the category desired by the user. Therefore, the user can intuitively understand the analysis information of the area that the user wants to observe.

Figure 11:
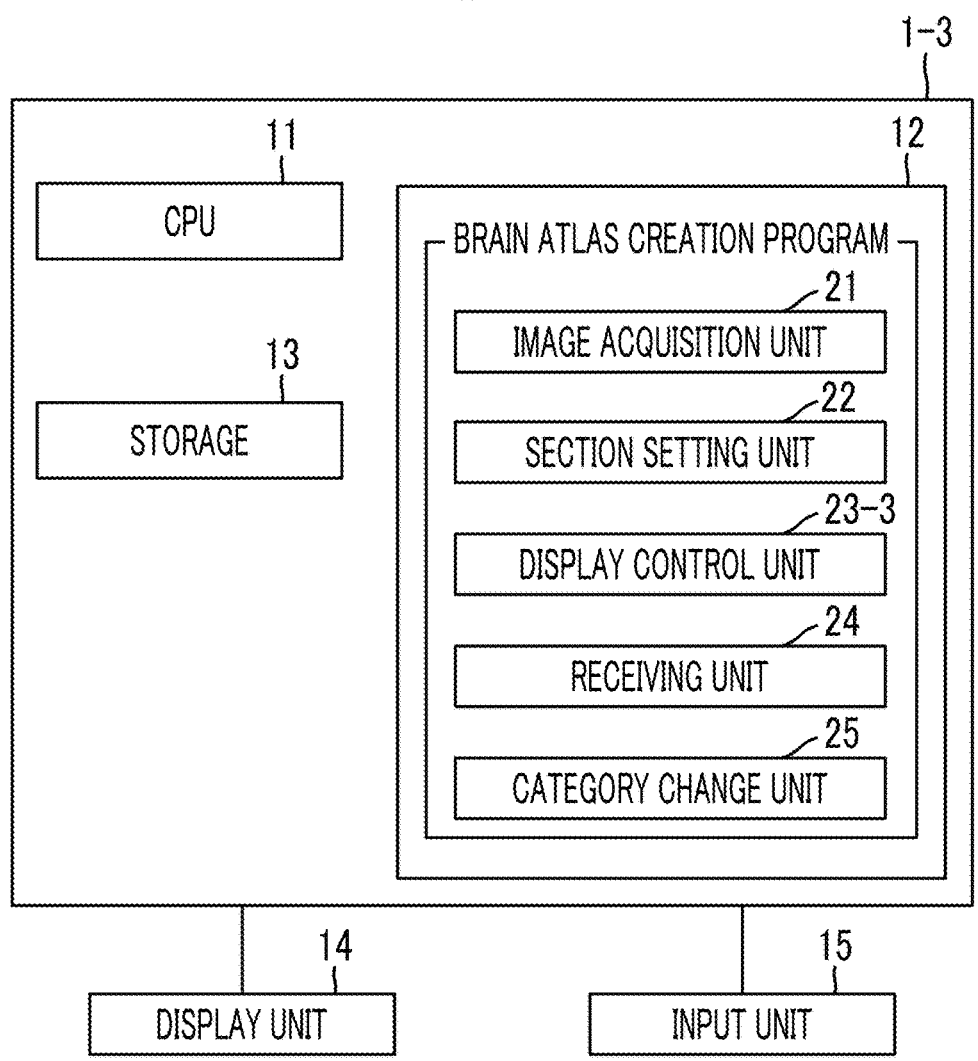
FIG. 11 is a schematic block diagram illustrating a configuration of a brain atlas creation apparatus according to a third embodiment of the present disclosure.

Next, a third embodiment of the present disclosure will be described with reference to the drawings. FIG. 11 is a diagram illustrating a schematic configuration of a brain atlas creation apparatus according to the third embodiment of the present disclosure. In addition, since the brain atlas creation apparatus according to the third embodiment has substantially the same configuration as the brain atlas creation apparatus according to the second embodiment, the same configurations are denoted by the same reference numerals and the description thereof will be omitted. Only different components will be described in detail.

As illustrated in FIG. 11, a brain atlas creation apparatus 1-3 according to the third embodiment comprises a category change unit 25 in addition to the configurations of the brain atlas creation apparatus 1-2 according to the second embodiment.

Figure 12:
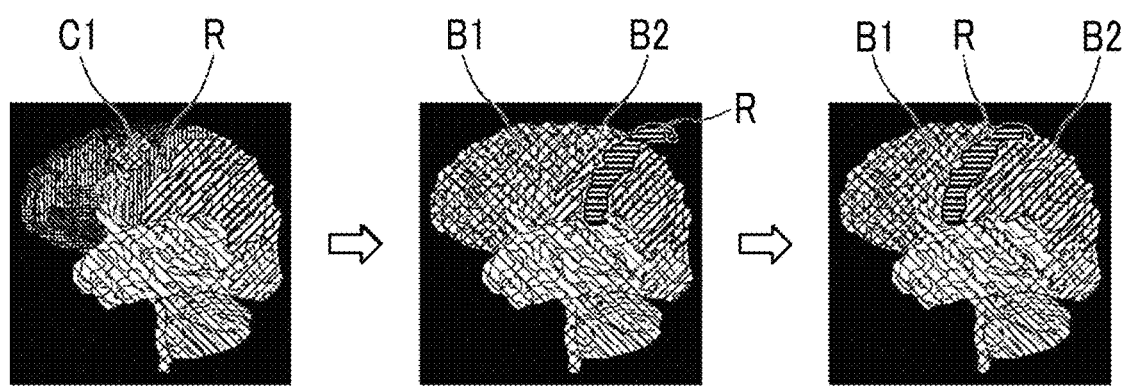
FIG. 12 is a diagram illustrating an operation of changing a category in the display of a brain atlas image.

The category change unit 25 changes a category higher than the category to which the section received by the receiving unit 24 belongs. FIG. 12 is a diagram illustrating an operation of changing the category in the display of the brain atlas image.

In a case in which the user operates the mouse as the input unit 15 to drag a precentral gyms section C1 in a state in which the area of the frontal lobe section B1 is displayed in the minor-category brain atlas image as illustrated in the left diagram of FIG. 12, the receiving unit 24 receives the precentral gyms section C1, and the display control unit 23-3 displays the medium-category brain atlas image as illustrated in the middle diagram of FIG. 12.

In a case in which the user operates the mouse as the input unit 15 to drag and drop the precentral gyms section C1 onto, for example, a parietal lobe section B2 set in the medium category, the category change unit 25 changes the category of the precentral gyms section C1 in the medium category from the frontal lobe section B1 to the parietal lobe section B2.

In addition, in a case in which the precentral gyms section C1 is dragged and the mouse is scrolled, the display control unit 23-3 displays a brain atlas image of a cross section different from the cross section displayed on the display unit 14.

As illustrated in the right diagram of FIG. 12, the display control unit 23-3 combines the area of the precentral gyms section C1 with the parietal lobe section B2 in the brain atlas image and displays the combined section in the atlas brain image. That is, the area of the precentral gyms section C1 which has been a portion of the frontal lobe section B1 is displayed as a portion of the parietal lobe section B2. Further, in the brain section list 31, the display control unit 23-3 changes a category higher than the category of the precentral gyms section C1, that is, the medium category from the frontal lobe section B1 to the parietal lobe section B2 and displays the section.

In addition, a method for changing the category by the category change unit 25 is not limited to the above. FIG. 13 is a diagram illustrating dragging and dropping in the brain section list. As illustrated in FIG. 13, the user operates the mouse as the input unit 15 to drag and drop, for example, the precentral gyms as the name of the brain section onto, for example, the parietal lobe which is the name of the brain section set in the medium category in the brain section list 31 displayed on the display unit 14 by the display control unit 23-3. Then, the category change unit 25 changes the category of the precentral gyms in the medium category from the frontal lobe to the parietal lobe. The display control unit 23-3 deletes the name of the precentral gyms displayed in the lower layer of the frontal lobe, newly adds the name of the precentral gyms to the lower layer of the parietal lobe, and displays the name of the precentral gyms. In this way, the category may be changed.

Further, another method for changing the category by the category change unit 25 will be described. FIG. 14 is a diagram illustrating a method for changing the category in the brain section list. As illustrated in FIG. 14, in a case in which the user operates the mouse as the input unit 15 to select, for example, the superior frontal gyms (left) as the name of the brain section in the brain section list 31 displayed on the display unit 14 by the display control unit 23-3, the receiving unit 24 receives the superior frontal gyms section. The display control unit 23-3 displays the name of a category higher than the category to which the superior frontal gyms section belongs, that is, the name of the medium category in the brain section list 31 displayed on the display unit 14. In addition, the display control unit 23-3 displays the name of the superior frontal gyms which is the section received by the receiving unit 24 so as to be highlighted as illustrated in FIG. 14.

Then, in a case in which the user changes the category name of the superior frontal gyms in the medium category from the frontal lobe to the parietal lobe, the category change unit 25 changes the category of the superior frontal gyms in the medium category from the frontal lobe to the parietal lobe. The display control unit 23-3 deletes the name of the superior frontal gyms displayed in the lower layer of the frontal lobe, newly adds the name of the superior frontal gyms to the lower layer of the parietal lobe, and displays the name of the superior frontal gyms. In this way, the category may be changed.

Further, the method for changing the category by the category change unit 25 is not limited to the above. FIG. 15 is a diagram illustrating an operation of changing the category in the brain section list. For example, the display control unit 23-3 displays the name of the section received by the receiving unit 24 so as to be highlighted and displays an edit menu 40 illustrated in FIG. 15 which is for changing the category higher than the category of the highlighted section. In the edit menu 40, a section name and label type 40a in the category higher than the category of the highlighted section is displayed. Then, in a case in which the user changes the section name and label type 40a and clicks "OK" 40b, the category change unit 25 may change the category to a category indicated by the changed section name and label type 40a. In addition, in a case in which the user wants to stop the change of category after changing the section name and label type 40a, the user may click "cancel" 40c.

Figure 16:
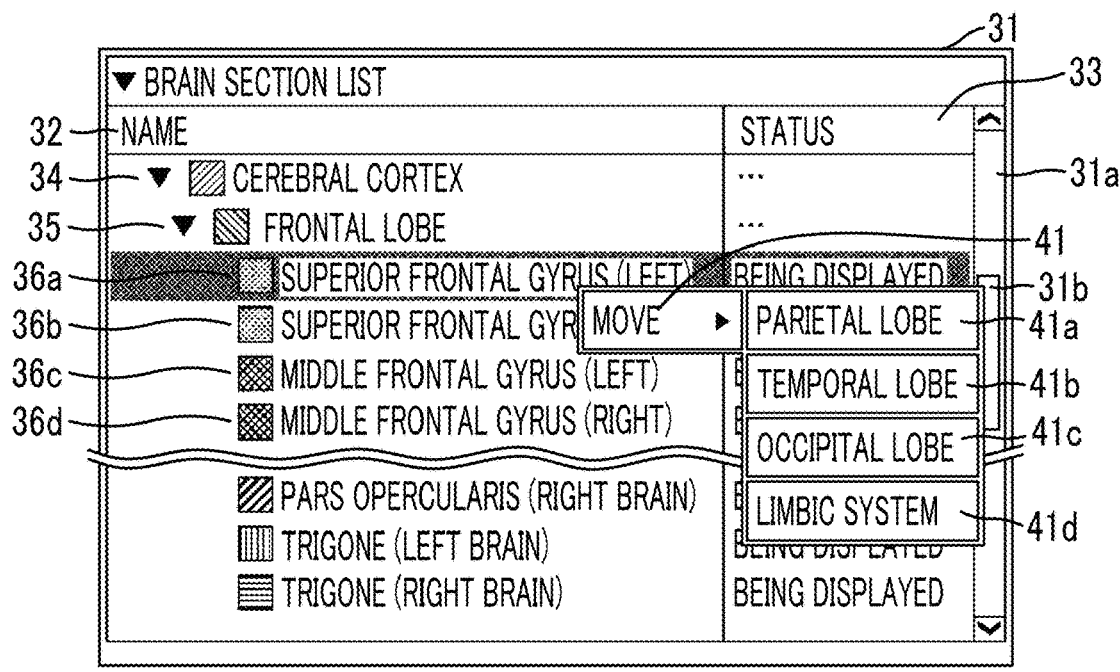
FIG. 16 is a diagram illustrating an operation of changing a category in the brain section list.

FIG. 16 is a diagram illustrating an operation of changing the category in the brain section list. In a case in which the user clicks a right button of the mouse as the input unit 15, for example, in the vicinity of the name of a section in the medium category on the brain section list 31, the display control unit 23-3 displays a new menu having an item of "move" 41 on the brain section list 31. In a case in which the user selects the "move" 41, the display control unit 23-3 further displays major category lists 41a to 41d in the menu. In a case in which the user clicks a desired category from the major category lists 41a to 41d, the category change unit 25 may change the major category of the section in the medium category received by the receiving unit 24 to the section in the clicked major category.

Figure 17:
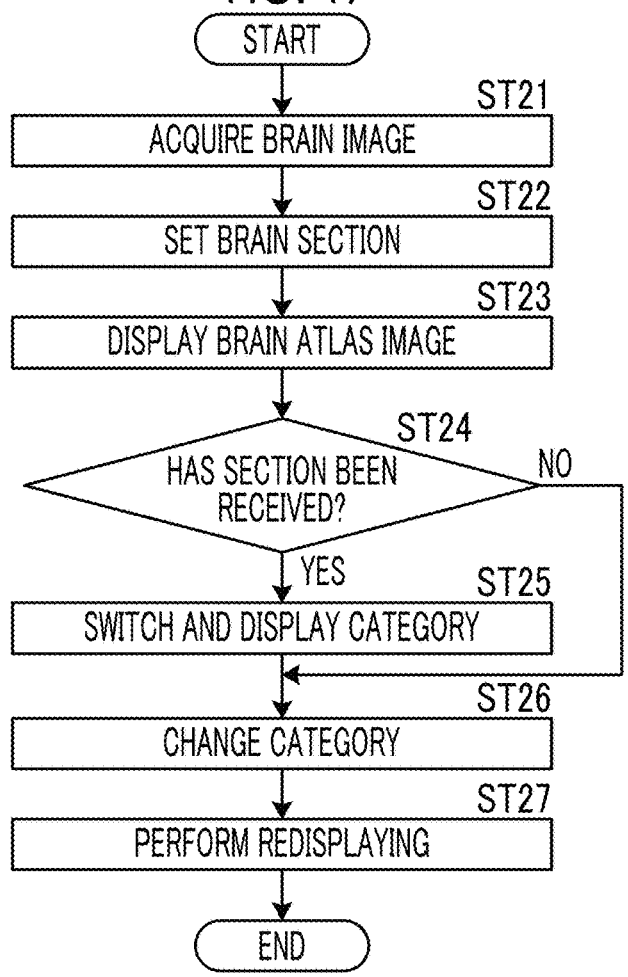
FIG. 17 is a flowchart illustrating a process performed in the third embodiment of the present disclosure.

Next, a process performed in the third embodiment will be described. FIG. 17 is a flowchart illustrating the process performed in the third embodiment. In addition, since a process in Steps ST21 to ST25 of the flowchart illustrated in FIG. 17 is the same as the process in Steps ST11 to ST15 of the flowchart illustrated in FIG. 10, the description thereof will be omitted for convenience.

As illustrated in FIG. 17, the category change unit 25 changes the category as described above (Step ST26). Then the display control unit 23-3 redisplays the brain atlas image and the brain section list 31, in which the change of the category has been reflected, on the display unit 14 (Step ST27). Then, a series of processes ends. In this way, a series of processes in the third embodiment is performed.

According to the third embodiment, the category of the brain section can be changed in any way. This makes it possible to visualize the category of the brain section set as desired by the user. In addition, the shape of each brain section varies depending on the subject. Therefore, in a case in which the user wants to perform analysis in a certain part, the category of the brain image to be observed is not necessarily set in the section desired by the user. According to the third embodiment, the brain sections can be set as desired by the user. Therefore, it is possible to improve the reliability of image diagnosis on the brain based on the analysis result.

Further, in the above-described embodiments, the category change unit may be configured to change the category only in adjacent sections. In this case, it is possible to prevent the areas belonging to the same category from being scattered.

Furthermore, in the above-described embodiments, for example, the following various processors can be used as the hardware structure of processing units performing various processes, such as the image acquisition unit 21, the section setting unit 22, and the display control unit 23. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

The disclosure of JP2018-184407 filed on Sep. 28, 2018 is incorporated herein by reference in its entirety.

All documents, patent applications, and technical standards described herein are incorporated herein by references to the same extent as the incorporation of the individual documents, patent applications, and technical standards by references are described specifically and individually.

What is claimed is:

1. A brain atlas creation apparatus comprising a processor configured to:
   acquire a brain image;
   classify a brain area in the brain image into a plurality of layers from a large category which is a higher layer to a small category which is a lower layer and set a brain section for each category;
   control to switch the brain image for each category and to display the brain image on a display unit;
   receive the brain section for each category of the brain image displayed on the display unit;
   display on the display unit the large category of the brain image; and
   receive a brain image switching instruction input to switch from the large category to the small category, wherein the large category comprises a plurality of sections of the large category, the small category comprises a plurality of sections of the small category which are in a section of the plurality sections of the large category.

2. The brain atlas creation apparatus according to claim 1, wherein the processor is further configured to:
   receive another brain image switching instruction input to switch from the small category to the large category.

3. The brain atlas creation apparatus according to claim 2, wherein the processor is configured to:
   control to display at least a portion of an area in the small category and at least a portion of the area in the large category on the display unit, and
   receive an input to drag and drop the received brain section in the small category onto a section set in the large category to change the small category of the received brain section to the large category.

4. The brain atlas creation apparatus according to claim 2, wherein the processor is configured to:
   control to display, on the display unit, a list of names of the sections of the brain for each category in a tree shape, and
   receive an input to drag and drop the name of a section selected in the list to the name of a section set in the large category, to which the section belongs, to change to the large category.

5. The brain atlas creation apparatus according to claim 2, wherein the processor is configured to:
   control to display, on the display unit, a name of the large category to which the received brain section belongs, and
   receive an input to change the name of the large category to change to the large category of the received brain section.

6. The brain atlas creation apparatus according to claim 2, wherein the processor is capable of changing to the large or small category only in adjacent sections.

7. The brain atlas creation apparatus of claim 1, wherein each section of the plurality of sections of the large category and each section of the plurality of sections of the small category are set according to an anatomical meaning of a brain.

8. The brain atlas creation apparatus of claim 1, wherein the processor is configured to receive the brain image switching instruction input to switch from the large category to the small category comprising:
   receive the brain image switching instruction input on the large category of the brain image to switch from the large category to the small category.

9. A brain atlas creation method, comprising:
   acquiring a brain image;
   classifying a brain area in the acquired brain image into a plurality of layers from a large category which is a higher layer to a small category which is a lower layer and setting a brain section for each category;
   performing control to switch the brain image for each classified category and to display the brain image on a display unit;
   receiving the section for each category of the brain image displayed on the display unit;
   displaying on the display unit the large category; and
   receiving a brain image switching instruction input to switch from the large category to the small category, wherein the large category comprises a plurality of sections of the large category, the small category comprises a plurality of sections in a section of the plurality sections of the large category.

10. A non-transitory computer-readable storage medium storing therein a brain atlas creation program that causes a computer to perform:
    acquiring a brain image;
    classifying a brain area in the acquired brain image into a plurality of layers from a large category which is a higher layer to a small category which is a lower layer and setting a brain section for each category;
    performing control to switch the brain image for each classified category and to display the brain image on a display unit;
    receiving the section for each category of the brain image displayed on the display unit;
    displaying on the display unit the large category; and
    receiving a brain image switching instruction input to switch from the large category to the small category, wherein the large category comprises a plurality of sections of the large category, the small category comprises a plurality of sections in a section of the plurality sections of the large category.

* * * * *